United States Patent [19]

McFearin, Jr.

[11] 4,007,216
[45] Feb. 8, 1977

[54] 2-METHOXY-4-METHYL-3-OXO-CYCLO-PENT-1-ENE-1,4-DICARBOXYLIC ACID ESTERS

[75] Inventor: Thurman Chestler McFearin, Jr., Odessa, Tex.

[73] Assignee: El Paso Products Company, Odessa, Tex.

[22] Filed: May 12, 1975

[21] Appl. No.: 576,742

Related U.S. Application Data

[62] Division of Ser. No. 426,021, Dec. 19, 1973, Pat. No. 3,922,296.

[52] U.S. Cl. .......................................... 260/468 K
[51] Int. Cl.² ........................................ C07C 69/74
[58] Field of Search ............................... 260/4.8 K

[56] References Cited

UNITED STATES PATENTS

| | | | |
|---|---|---|---|
| 2,865,962 | 12/1958 | Krimon et al. | 260/586 |
| 3,870,711 | 3/1975 | Martel et al. | 260/240 |

OTHER PUBLICATIONS

March, Advanced Org. Chem., pp. 794–799 (1967).
Tonari, et al., Nippon Nogei Kagoku Kaishi, 44, 46, 1970.

*Primary Examiner*—Robert Gerstl
*Attorney, Agent, or Firm*—Depaoli & O'Brien

[57] ABSTRACT

The disclosure relates to a novel process for the preparation of 3-alkyl-cyclopentane-1,2-diones and, in particular, to a novel process for the preparation of 3-methyl-cyclopentane-1,2-dione also known as Maple Lactone. The process comprises condensation of esters of glutaric acid and oxalic acid in a polar aprotic solvent in the presence of an alkali metal alkoxide to form 3,5-dicarboalkoxy-cyclopentane-1,2-dione dialkali metal salts, alkylating said salts with an alkylating agent to form a 2-alkoxy-3,5-dicarboalkoxy-5-alkyl-cyclopent-1-ene removing said solvent therefrom, and hydrolyzing the remainder with a mineral acid to form a 3-alkyl-cyclopentane-1,2-dione.

1 Claim, No Drawings

2-METHOXY-4-METHYL-3-OXO-CYCLOPENT-1-ENE-1,4-DICARBOXYLIC ACID ESTERS

This is a division, of application Ser. No. 426,021 filed Dec. 19, 1973, now U.S. Pat. No. 3,922,296.

BACKGROUND OF THE INVENTION

1. Field of the Invention

The present invention is directed to a novel process for the preparation of 3-alkyl-cyclopentane-1,2-diones and in particular, to a novel process for the preparation of 3-alkyl-cyclopentane-1,2-diones via the intermediates 2-alkoxy-3,5-dicarboalkoxy-5-alkyl-cyclopent-2-ene-1-ones by the condensation of esters of glutaric acid and oxalic acid in a polar aprotic solvent in the presence of an alkali metal alkoxide to form 3,5-dicarboalkoxy-cyclopentane-1,2-dione dialkali metal salts, alkylating said salts with an alkylating agent to form a 2-alkoxy-3,5-dicarboalkoxy-5-alkyl-cyclopent-2-ene-1-one, removing said solvent therefrom, and hydrolyzing the remainder to form a 3-alkyl-cyclopentane-1,2-dione. In particular, the invention contemplates the novel process defined above for the preparation of 3-methyl-cyclopentane-1,2-dione, also known as Maple Lactone, which finds immediate and practical utility as a flavoring agent in the manufacture of synthetic maple syrup.

2. Description of the Prior Art

It is generally recognized that 3-alkyl-cyclopentane-1,2-diones are materials having sweet characteristic flavors reminiscent of walnuts and which, heretofore, have been employed as flavoring additives in a variety of food products. In particular, 3-methyl-cyclopentane-1,2-dione is a white crystalline solid which has been found to be useful as the primary flavoring agent in the preparation of synthetic maple syrup and has come to be known as Maple Lactone.

Because of the well-accepted use of this product and its analogous compounds, the art has been interested in developing economical and commercial processes for the preparation of the 3-alkyl-cyclopentane-1,2-diones from readily available starting materials. However, the processes known heretofore in the patent and technical literature suffer serious technical deficiencies which render them unsuitable for development into economical, commercially feasible processes.

One such patent, which relates to products of this type, is U.S. Pat. No. 3,865,962 which teaches the preparation of these compounds by reaction of an alkyl acrylate with an alkali metal salt of an alkyl alkoxalylpropionate and decarboxylating the resulting cyclic compound. A further method is provided for preparation of analogous products in U.S. Pat. No. 3,652,643, specifically the preparation of 2-hydroxy-3-lower alkyl-cyclopent-2-en-1-ones by cyclization of dialkyladipate to 2-carbo-alkoxy-cyclopentan-1-one, alkylation thereof to 2-lower alkyl 2-carboalkoxycyclopentan-1-one, introducing an appropriate halogen gas into an anhydrous reaction inert organic solvent solution of said 2-lower alkyl-2-carboalkoxycyclopentan-1-one producing a product 2-lower alkyl-2 carbomethoxy-5,5-dibromo or dichloro cyclopentane-1-one, the acid hydrolysis of the latter compound to yield the final product.

In addition, U.S. Pat. No. 3,518,296 to Bucourt et al. teaches the preparation of 2-alkyl-cyclopentane-1,3 diones by the process of reacting a beta-keto ester with an alkaline cyclizing agent, saponifying the resultant 2-lower alkyl-4-carboxylate-cyclopentane-1,3-dione, decarboxylating the resultant 2-lower alkyl-4-carboxy-cyclopentane-1,3-dione, and recovering the 2-alkyl cyclopentane-1,3-diones.

Further, U.S. Pat. No. 3,349,130 also to Bucourt teaches a process for preparing the 2-alkyl-cyclopentane-1,3 diones which comprises cyclizing a lower alkyl ester of 5-lower alkyl-levulinic acid in the presence of an alkali metal tertiary alcoholate in an aprotic solvent to obtain a corresponding 2-lower alkyl cyclopentane-1,3-diones.

Another U.S. Pat. No. 3,671,589 teaches the preparation of 2-alkyl cyclopentane-1,3-dione by the reaction of succinic anhydride with an appropriate carboxylic acid anhydride in the presence of aluminum chloride and in an inert organic solvent. The acid hydrolysis of the latter product yields the final product. In addition, each of the above mentioned U.S. patents also disclose various other prior art processes for the preparation of compounds of this type.

None of the above processes, however, are considered to be particularly pertinent to the process of the instant invention.

Among the literature references which relate to the process of the instant invention are articles by Hesse et al., *Liebig. Ann.* 563, pp 31–53 (1949) and Gianturco et al., *tetrahedron*, 19, pp 2031–2049, (1963). Aside from the fact that the starting materials of the instant invention are mentioned by Gianturco et al. the similarity between the process of the instant invention and the processes mentioned by Hesse et al. and Gianturco et al. is remote.

SUMMARY OF THE INVENTION

Accordingly, an object of this invention resides in the provision of a novel process for the preparation of 3-alkyl-cyclopentane-1,2-diones which is both economical and commercially feasible and which avoids or overcomes the serious disadvantages of prior art processes.

A further object of this invention resides in the provision of means for producing 2-alkoxy-3,5-dialkoxy-5-alkyl-cyclopent-2-ene-1-ones as intermediates for the preparation of 3-alkyl-cyclopentane-1,2-diones.

A still further object of this invention resides in the provision of a multi-step procedure for the preparation of 3-alkyl-cyclopentane-1,2-diones which eliminates the necessity for isolation of intermediates.

In achieving the foregoing objects and advantages of the invention there is provided a process for the preparation of 3-alkyl-cyclopentane-1,2-diones which comprises condensing a dialkyl ester of oxalic acid with a dialkyl ester of glutaric acid in a polar aprotic solvent in the presence of an alkali metal alkoxide and at a temperature sufficient to effect condensation to form 3,5-dicarboalkoxy cyclopentane-1,2-dione dialkali metal salt, reacting said salt, without isolation, with an alkylhalide under alkylation conditions by contact with at least an equimolar amount of the alkylhalide to produce 2-alkoxy-3,5-dicarboalkoxy-5-alkyl-cyclopent-2-ene-1-one, removing said aprotic solvent and hydrolyzing said 2-alkoxy-3,5-dicarboalkoxy-5-alkyl-cyclopent-2-ene-1-one by heating with 10–30 percent aqueous mineral acid to produce a 3-alkyl cyclopentane-1,2-dione.

In carrying out the process of invention it is preferred that the polar aprotic solvent have a dipole moment of at least 1.5.

DESCRIPTION OF PREFERRED EMBODIMENTS

As pointed out above, this invention relates to the preparation of 3-alkyl-cyclopentane-1,2-diones which may be represented by the following general formula:

A.

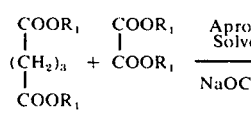 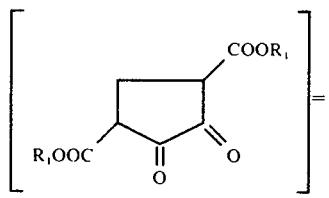

B.

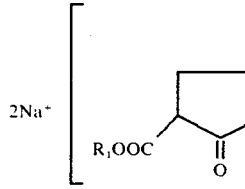 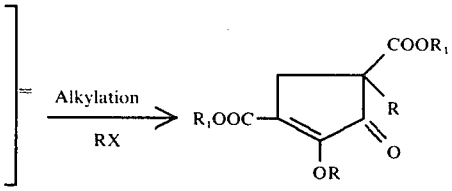

C.

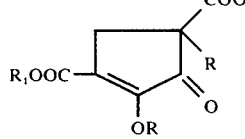 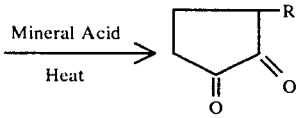

I. 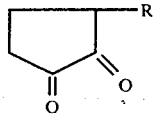

wherein R is alkyl of 1 to 5 crbon atoms but is preferably methyl.

It is to be understood, of course, that the compound of formula I also exists as the 1-hydroxy tautomer as illustrated by the following equation:

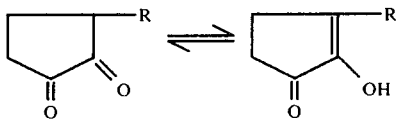

Thus the invention is inclusive of both products.

According to the process of this invention, these compounds are prepared by condensing a dialkyl ester of glutaric acid with a dialkyl ester of oxalic acid, in a polar aprotic solvent, in the presence of an alkali metal alkoxide and at temperatures sufficient to effect condensation of said esters to form a first reaction mixture containing 3,5-dicarboalkoxy cyclopentane-1,2-dione dialkali metal salt, contacting said first reaction mixture with at least an equimolar amount of an alkyl halide under alkylating conditions to produce a second reaction mixture containing 2-alkoxy-3,5-dicarboalkoxy-5-alkyl-cyclopent-2-ene-1-one, removing said aprotic solvent from said second reaction mixture and hydrolyzing said 2-alkoxy-3,5-dicarboalkoxy-5-alkyl-cyclopent-2-ene-1-one by heating with a 10 to 30 percent aqueous mineral acid solution to produce a 3-alkyl-cyclopentane-1,2-dione as represented by formula I, above.

While not wishing to be bound by any particular theory or mechanism of reaction, it is believed that the following series of steps illustrates the reaction scheme in which the alkali metal alkoxide is $NaOCH_3$:

In the above equations R is alkyl as defined in formula I, $R_1$ is lower alkyl of 1–7 carbon atoms, preferably methyl, and X is halogen, preferably bromine or chlorine.

This initial reaction (A) is a condensation of approximately equimolar amounts of the simple dibasic acid esters of oxalic acid and glutaric acid in the presence of a polar aprotic solvent. The reaction may be carried out at a temperature ranging from room temperature up to 120° C., and preferably from 50°–120° C. and in the presence of an alkali metal alkoxide which is present in a molar excess and preferably with about 2 moles of the alkali metal alkoxide for each mole of reactants. It should also be conducted free of oxygen or in the presence of an inert gas such as nitrogen. After the reaction is completed, the product is stirred vigorously, and any alcohol formed in the reaction is allowed to distill, but it is not necessary to remove all the alcohol formed. Without the addition of external heat, it will be found that the reaction is complete in about three hours.

In the reaction of equation A, the alkali metal alkoxide used is preferably alkali metal methoxide, but other materials may be used with the same results, including alkali-metal n-butoxides, ethoxides, n-propoxide or mixtures thereof. The preferred alkali metal is sodium, but potassium or lithium may also be used. Sodium methoxide and sodium ethoxide are highly preferred reagents.

One of the main features of the process of this invention is the use of the aprotic solvent in step (A), and as the aprotic solvent there may be used such solvents as dimethylformamide, dimethylsulfoxide, dimethylacetamide, sulfolane and the like, or mixtures thereof. The highly preferred process of this invention uses an aprotic solvent which has a high dipole moment, that is a dipole moment exceeding 1.5, and the above listed solvents fall within this range. Dimethylformamide is the aprotic solvent of choice.

While it is possible to isolate intermediate products from step A of the process, according to the scheme of this invention it is not necessary or economical to do so. Thus, the final mixture from the initial reaction, which is a thick light-brown solution that becomes a slurry after distillation or other removal of the alcohol formed, may be reacted as is without removal of aprotic solvent or purification of the intermediate in the second step, alkylation step (B).

In step (B), the 3,5-dicarboalkoxy cyclopentane-1,2-dione dialkali metal salt is alkylated to form a 2-alkoxy-3,5-dicarboalkoxy-5-alkyl-cyclopent-2-ene-1-one. According to the process of the invention, the product from step (A) is reacted with at least an equimolar amount and preferably a slight molar excess of an alkyl halide, preferably an alkyl halide of the formula RX in which R is alkyl of 1-5 carbon atoms, and X is bromine or chlorine, with vigorous agitation while the alkyl halide is bubbled or otherwise added to the crude slurry at as rapid a rate as possible except that no alkyl halide should be eluted from the reactor during the addition. The alkylation reaction is carried out at about 70°-120° C., and a batch process would require about 1-3 hours by use of external heat. If external heat is not employed and the heat of reaction will cause the alkylation to proceed at about 40°-60° C and require about 5-7 hours for completion. The alkylation agents of choice are methyl, ethyl, n-propyl or n-butyl halides with the halide being bromide or chloride. However, methyl bromide and ethyl bromide are highly preferred.

As this reaction proceeds and alkylation occurs, the contents of the reactor gradually become less viscous and dark brown with crystals of alkali metal halide settling out when agitation ceases. At this point, the aprotic solvent is stripped from the reaction at temperatures below about 120° C and preferably under vacuum. The crude dark-brown mixture, which contains primarily the 2-alkoxy-3,5-dicarboalkoxy-5-alkyl-cyclopent-2-ene-1-one and alkali metal halide can be subjected to hydrolysis with or without purification. If it is desired to purify this intermediate, the dark-brown mixture is first washed with water to remove the alkali metal halide and vacuum distilled at temperatures of less than 150° C to obtain the organic phase as a light yellow viscous oil.

In step (C) of the process, this intermediate product either as the crude dark-brown mixture or as the light viscous oil, is then hydrolyzed by reaction with about 5-40 weight percent, preferably 10-30 weight percent, aqueous solution of a mineral acid. The preferred mineral acid is sulfuric acid, but other acids such as phosphoric acid and hydrochloric acid may be used if desired. In conducting the process, the reactant and an excess of the mineral acid are heated at reflux with vigorous agitation for about 3 to about 30 hours, preferably 6 to 30 hours. A larger excess of acid used in the reaction will reduce the time required for effecting the hydrolysis. Also the higher alkyl esters require stronger acid solutions and longer periods to complete the hydrolysis. Completion of the reaction may be determined by analysis, e.g. by gas chromatography.

On completion of the reaction, the final product is isolated from the resulting solution by filtering to remove any tarry materials and by extracting with a solvent, e.g. an alkyl acetate, to remove the soluble product.

As a result of the above described process, the yields of final product are 70-75 percent of the theoretical based on the dialkyl esters employed as initial starting materials.

As pointed out above, the final products of this invention are useful as flavoring agents for foods, beverages, tobaccos, confections and blending perfumes, and a specific compound, Maple Lactone, finds outstanding use as the preferred substitute for the flavor of maple in synthetic maple syrup.

The following Examples will serve to illustrate the practice of the invention.

EXAMPLE 1

3-Methyl Cyclopentane-1,2-Dione (2-Hydroxy-3-methyl cyclopent-2-ene-1-one)

A 5-liter three-necked round bottom flask is fitted with a thermometer and nitrogen inlet tube, a mechanical stirrer, and a ten-tray Oldershaw column with a condenser and take-off head. The flask is purged with dry nitrogen and charged with two liters of dry dimethylformamide, 292 grams (2 moles) diethyl oxalate, 320 grams (2 moles) dimethyl glutarate, and 240 grams (4.44 moles) of sodium methoxide. With the addition of sodium methoxide, the temperature rose to approximately 50° C. Continuing the nitrogen purge and while stirring, the pot temperature is taken to about 110° C. During this time the thick, light-brown solution is stirred vigorously and the methanol and ethanol formed during the reaction is allowed to distill. It was not necessary to remove all of the alcohol formed during the reaction. The reaction is complete at 110° C. pot temperature in about 30 minutes. The pot contains the condensation products:

3,5-Dicarbomethoxy cyclopentane-1,2-dione disodium salt, 3,5-Dicarboethoxy cyclopentane-1,2-dione disodium salt, 3-Carbomethoxy-5-carboethoxy cyclopentane-1,2-dione disodium salts, hereafter referred to as 3,5-dicarboalkoxy cyclopentane-1,2-dione disodium salt in Example 1.

Into the thick, light-brown slurry of 3,5-dicarboalkoxy cyclopentane-1,2-dione disodium salt formed by the condensation reaction of the alkyl esters of oxalic acid and glutaric acid as described in the above paragraph, is bubbled 422 grams (4.44 moles) of methyl bromide with vigorous stirring at as rapid a rate as possible, provided no methyl bromide is eluted from the pot. This alkylation step is conducted at a temperature of about 70°-100° C. in 2 hours, using external heat. Without external heat, and the condensed esters at room temperature, alkylation will proceed at a temperature of 45°-55° C. When about one liter of dimethylformamide is removed, the pot contents are filtered to remove the majority of the sodium bromide formed during the alkylation step. When all the dimethylformamide is removed, the crude dark brown mixture (1000 grams) contains mostly:

2-methoxy-3,5-dicarbomethoxy-5-methyl cyclopent-2-ene-1-one, 2-methoxy-3,5-dicarboethoxy-5-methylcyclopent-2-ene-1-one, 2-methoxy-3-carbomethoxy-5-carboethoxy-5-methyl-cyclopent-2-ene-1-one, 2-methoxy-5-carbomethoxy-3-carboethoxy-5-methyl-cyclopent-2-ene-1-one
(referred to hereafter in Example 1 as 2-methoxy-3,5-dicarboalkoxy-5-methyl cyclopent-2-ene-1-one) and a small amount of sodium bromide.

The crude dark brown mixture of 2-methoxy-3,5-dicarboalkoxy-5-methyl cyclopent-2-ene-1-one is mixed with 2 liters of 10% sulfuric acid and heated at reflux with vigorous stirring for 3 hours. The resulting brown solution is cooled to about 50° C. and filtered to remove small amounts of black tars. The filtrate is cooled to room temperature and crystals (about 90 grams) of 3-methyl cyclopentane-1,2-dione removed by filtration. The filtrate is extracted with three 300-ml portions of ethyl acetate to remove the soluble product. The product crystals removed by filtration are added to the ethyl acetate extracts and washed with a saturated sodium bicarbonate solution, then distilled water. The ethyl acetate phase is heated on a steam bath to remove ethyl acetate, leaving the crude 3-methyl cyclopentane-1,2-dione. Yields overall are 160–165 grams or 70–75% of theoretical from the esters. The crude crystals of the product are recrystallized from ethyl acetate to give a material of M.P. 102°–105° C. whose molecular weight is 112.

EXAMPLE 2

The condensation reaction of dimethyl glutarate and diethyl oxalate with sodium methylate, being exothermic, is repeated without adding external heat. The time required for condensation is about three hours during which time the pot temperature is 40° C., when using sodium methylate. In this example, no methanol is removed from the reaction mixture. Complete condensation is indicated by a very thick, light-brown reaction mixture and confirmed by gas chromatographic analysis showing the absence of the starting esters of glutaric and oxalic acid. Subsequent alkylation and hydrolysis of the condensation product to 3-methyl-cyclopentane-1,2-dione is achieved by the procedure outlined in Example 1.

EXAMPLE 3

3-Methyl Cyclopentane-1,2-Dione (2-Hydroxy-3-methyl cyclopent-2ene-1-one)

The condensation reaction of equimolar amounts of dimethyl glutarate and dimethyl oxalate with sodium methylate is repeated according to the procedure of Example 1.

Alkylation of the 3,5-dicarbomethoxy cyclopentane-1,2-dione disodium salt with methyl bromide is accomplished also by the same procedure of Example 1.

Removal of the solvent dimethylformamide is accomplished in the same manner as described in Example 1, leaving a dark brown mixture and containing mostly 2-methoxy-3,5-dicarbomethoxy-5-cyclopent-2-ene-1-one which may be purified by first washing with water to remove the sodium bromide and vacuum distilling the organic phase at a temperature of 135°–139° C. using a 20-tray Oldershaw column. The distilled product is a light yellow viscous oil that may be subsequently hydrolyzed to a very pure 3-methyl cyclopentane-1,2-dione with 10% sulfuric acid by the procedure of Example 1.

EXAMPLE 4

The procedures of Example 1 and Example 2 are repeated using the following esters of oxalic acid and glutaric acid and mixtures thereof.

| Oxalic Acid Esters | Glutaric Acid Esters |
|---|---|
| Dimethyl oxalate | Dimethyl glutarate |
| Diethyl oxalate | Diethyl glutarate |
| Di-n-propyl oxalate | Di-n-propyl glutarate |
| Di-n-butyl oxalate | Di-n-butyl glutarate |

EXAMPLE 5

3-Methyl Cyclopentane-1,2-Dione (2-Hydroxy-3-methyl cyclopent-2-ene-1-one)

The procedure of Example 1 is repeated using dimethyl acetamide in place of dimethylformamide as the polar aprotic solvent. Subsequent hydrolysis of the 2-methoxy-3,5-dicarboalkoxy-5-methyl cyclopent-2-ene-1-one by the method of Example 1 yields 3-methyl cyclopentane-1,2-dione.

EXAMPLE 6

3-Methyl Cyclopentane-1,2-Dione (2-Hydroxy-3-methyl cyclopent-2-ene-1-one)

The procedure of Example 1 is repeated using dimethyl sulfoxide in place of dimethylformamide as the polar aprotic solvent. Subsequent hydrolysis of the 2-methoxy-3,5-dicarboalkoxy-5-methyl cyclopent-2-ene-1-one by the method of Example 1 yields 3-methyl cyclopentane-1,2-dione.

EXAMPLE 7

The condensation products of dimethyl glutarate and diethyl oxalate, referred to and prepared by the procedure in Example 1 as 3,5-dicarboalkoxy cyclopent-2-ene-1-one disodium salts, are alkylated with ethyl bromide by mixing with 4.44 moles of the ethyl bromide at an alkylation temperature of 40°–100° C. under alkylating conditions. The pot contents gradually became less viscous and dark brown with crystals of sodium bromide settling out when stirring ceased. The solvent dimethylformamide is stripped at 20 mm Hg and a temperature of 70°–80° C. by the procedures of Example 1. The crude dark brown mixture contains the four 2-ethoxy-3,5-dicarbo alkoxy-5-ethyl cyclopent-2-ene-1-one compounds referred to in Example 1.

EXAMPLE 8

3-Ethyl-Cyclopentane-1,2-Dione (2-Hydroxy-3-ethyl cyclopent-2-ene-1-one)

The crude dark brown mixture of the four products of Example 7 is mixed with 2 liters of 20% sulfuric acid and heated at reflux with vigorous stirring for about 8 hours. The resulting solution is cooled to about 50° C. and filtered to remove small amounts of tars. The filtrate is cooled to room temperature and the crystals of 3-ethyl cyclopentane-1,2-dione removed by filtration. The filtrate is extracted with two 400 ml portions of ethyl acetate to remove the soluble product. The product 3-ethyl cyclopentane-1,2-dione is purified by the procedure described in Example 1.

EXAMPLE 9

3-Butyl-Cyclopentane-1,2-Dione (2-Hydroxy-3-butyl cyclopent-2-ene-1-one)

The condensation products of dimethyl glutarate and diethyl oxalate, referred to and prepared by the procedure in Example 1 as 3,5-dicarbo alkoxy cyclopent-2-ene-1-one disodium salts, are alkylated with butyl bromide by mixing with 4.44 moles of the butyl bromide at an alkylation temperature of 75°–100° C. under alkylating conditions.

Subsequent removal of dimethylformamide solvent by the procedure of Example 1 and acid hydrolysis yields the 3-butyl-cyclopentane-1,2-dione compound.

EXAMPLE 10

3-Methyl Cyclopentane-1,2-Dione (2-Hydroxy-3-methyl cyclopent-2-ene-1-one)

The condensation products of dimethyl glutarate and diethyl oxylate, referred to and prepared by the procedure in Example 1 as 3,5-dicarboalkoxy cyclopent-2-ene-1-one disodium salts, are alkylated with dimethyl sulfate by mixing with 4.44 moles of the dimethyl sulfate at an alkylation temperature of 40°–100° C. under alkylating conditions. Subsequent removal of dimethylformamide and acid hydrolysis yields 3-methyl-cyclopentane-1,2-dione.

EXAMPLE 11

3-Methyl-Cyclopentene-1,2-Dione (2-Hydroxy-3-methyl-cyclopent-2-ene-1-one)

The condensation products of dimethyl glutarate and diethyl oxalate, referred to and prepared by the procedure in Example 1 as 3,5-dicarboalkoxy cyclopent-2-ene-1-one disodium salts, are alkylated with methyl chloride at an alkylation temperature of 40°–100° C. under alkylating conditions. Subsequent removal of dimethylformamide and acid hydrolysis yields 3-methyl-cyclopentane-1,2-dione.

While the invention has been described by way of specific examples it is not to be limited thereby and it is manifestly obvious that numerous modification and variations of the invention will occur to those skilled in the art without departing from the spirit and scope of the invention. Thus, the invention is not to be limited except by the scope of the appended claims.

What is claimed is:

1. As a composition of matter 2-methoxy-3,5-dicarboalkoxy-5-methylcyclopent-2-ene-1-one.

* * * * *